US010611852B2

(12) United States Patent
Liu et al.

(10) Patent No.: US 10,611,852 B2
(45) Date of Patent: Apr. 7, 2020

(54) INSULIN-LIPID COMPLEX, PREPARATION METHOD THEREFOR, AND PREPARATION THEREOF

(71) Applicant: Institute of Materia Medica, Chinese Academy of Medical Sciences, Beijing (CN)

(72) Inventors: Yuling Liu, Beijing (CN); Cuiping Zhou, Beijing (CN); Zhihui Song, Beijing (CN); Lin Li, Beijing (CN); Hongliang Wang, Beijing (CN); Xuejun Xia, Beijing (CN); Renyun Wang, Beijing (CN); Wujun Dong, Beijing (CN); Dujia Jin, Beijing (CN)

(73) Assignee: INSTITUTE OF MATERIA MEDICA, CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 15/895,282

(22) Filed: Feb. 13, 2018

(65) Prior Publication Data

US 2018/0171031 A1 Jun. 21, 2018

Related U.S. Application Data

(62) Division of application No. 13/810,098, filed as application No. PCT/CN2011/077152 on Jul. 14, 2011, now abandoned.

(30) Foreign Application Priority Data

Jul. 14, 2010 (CN) .......................... 2010 1 0226102

(51) Int. Cl.
| | |
|---|---|
| *C07K 17/02* | (2006.01) |
| *A61K 9/107* | (2006.01) |
| *A61K 9/14* | (2006.01) |
| *A61K 47/24* | (2006.01) |
| *C07K 14/62* | (2006.01) |
| *A61K 38/00* | (2006.01) |
| *A61K 9/127* | (2006.01) |

(52) U.S. Cl.
CPC ............ *C07K 17/02* (2013.01); *A61K 9/1075* (2013.01); *A61K 9/127* (2013.01); *A61K 9/145* (2013.01); *A61K 47/24* (2013.01); *C07K 14/62* (2013.01); *A61K 38/00* (2013.01)

(58) Field of Classification Search
None
See application file for complete search history.

(56) References Cited

U.S. PATENT DOCUMENTS

| 4,614,730 A | 9/1986 | Hansen et al. |
| 5,858,398 A | 1/1999 | Cho |
| 6,258,377 B1 | 7/2001 | New et al. |
| 2008/0279815 A1 | 11/2008 | Ceve |
| 2013/0338064 A1 | 12/2013 | Liu et al. |

FOREIGN PATENT DOCUMENTS

| CN | 101524349 A | 9/2009 | |
| EP | 2594281 A1 | 5/2013 | |
| WO | 9011780 A1 | 10/1990 | |
| WO | 9513795 A1 | 5/1995 | |
| WO | 2010060667 A1 | 6/2010 | |
| WO | WO-2010060667 A1 * | 6/2010 | ........... A61K 9/1075 |

OTHER PUBLICATIONS

Sarmento et al. "Oral insulin delivery by means of solid lipid nanoparticles", International Journal of Nanomedicine, 2007, vol. 2, No. 4, pp. 743-749.
Cui et al. "Biodegradable nanoparticles loaded with insulin-phospholipid complex for oral delivery: Preparation, in vitro characterization and in vivo evaluation", Journal of Controlled Release, 2006, vol. 114, No. 2, pp. 242-250.
Canadian Office Action dated May 12, 2017 issued in corresponding Canadian Patent Application No. 2,805,325.
Kisel et al. "Liposomes with phosphatidylethanol as a carrier for oral delivery of insulin: Studies in the rat", International Journal of Pharmaceutics, 2001, vol. 216, pp. 105-114.
Fricker et al. "Phospholipids and lipid-based formulations in oral drug delivery", Pharmaceutical Research, Aug. 2010, vol. 27, No. 8, pp. 1469-1486.
International Search Report dated Oct. 27, 2011 issued in PCT/CN2011/077152.
Canadian Office Action dated Apr. 3, 2019 issued in Canadian Patent Application No. 2,805,325.
Semalty A. et al., "Pharmacosomes: the lipid-based new drug delivery system", Exper Opin Drug Deliv., (2009), 6:6, pp. 599-612 https://doi.org/10.1517/17425240902967607.

* cited by examiner

*Primary Examiner* — Vanessa L Ford
*Assistant Examiner* — Sandra E Dillahunt
(74) *Attorney, Agent, or Firm* — Scully Scott Murphy & Presser, P.C.

(57) ABSTRACT

Provided are an insulin-lipid complex, a preparation method thereof, and a formulation thereof. The insulin-lipid complex is prepared by compounding insulin and a lipid material in an organic solvent system containing a low boiling point acid, and drying. The mass ratio of insulin to the lipid material is 1:3~1:20. An oil solution of the insulin-lipid complex and vesicles containing insulin are further provided.

10 Claims, 1 Drawing Sheet

INSULIN-LIPID COMPLEX, PREPARATION METHOD THEREFOR, AND PREPARATION THEREOF

CROSS REFERENCE TO RELATED APPLICATIONS

The present application is a divisional application of U.S. Ser. No. 13/810,098, filed on Sep. 3, 2013, which is the national phase of PCT/CN2011/077152, filed on Jul. 14, 2011, which claims priority of Chinese Application No. 201010226102.7 filed on Jul. 14, 2010, the entire contents of which are incorporated herein by reference.

TECHNICAL FIELD

The invention relates to an insulin-lipid complex and a method for the preparation thereof. The invention also relates to an oil solution containing the insulin-lipid complex, the use thereof in the preparation of formulations for sustained-released injection and non injection administration, and the use of novel vesicles (liposomes) that contain the insulin-lipid complex in the preparation of a formulation for non-injection administration. The invention generally relates to the field of medicine.

PRIOR ART

1. The Research Progress and Background of Lipid Complexes 1.1 Structural Characteristics and Formation Mechanisms of the Complexes Phospholipid complexes were discovered by the Italian scholar, Bombardelli, in the study of liposomes. Early research on phospholipid complexes was mostly on flavonoid containing phenolic hydroxyls or polyphenols. Subsequently, further research proved that in addition to phenolic hydroxyls, some polar groups such as alcoholic hydroxyl groups, amide groups, or carbonyl groups might react with the hydrophilic head of phospholipids or other lipid materials (such as cholesterol, sodium cholate, etc.) to form a complex spheroid by intermolecular hydrogen bonding or VDW (Van der Waals' force). Both hydrophilic drugs and lipophilic drugs can form lipid complex as long as they contain a polar group for forming the complex. Formation of a lipid complex can significantly improve the lipophilicity and oil solubility of drugs.

As FIG. 2 shows, the composition and structure of phospholipid complexes are markedly different from vesicles (also known as liposomes), which are also composed of phospholipids. A liposome is an artificially-prepared vesicle composed of a lipid bilayer with the hydrophilic heads of the phospholipid molecules facing outward and the hydrophobic tails facing inward. A phospholipid complex is a lipophilicity spheroid, fixed by the interactions between the polar groups of active ingredients and the hydrophilic heads of phospholipids. The hydrophilic heads are encapsulated, whereas the hydrophobic tails do not participate in the recombination reaction and can move freely.

A liposome vesicle may be formed by hundreds or thousands of phospholipid molecules, with the hydrophilic heads of phospholipids constituting the outer and inner layers of the lipid bilayer, and with the hydrophobic tails in the middle interlayer. Lipophilic drugs can be encapsulated in the interlayer of a bilayer membrane (blue square in the figure), with high and stable entrapment efficiency, and are not prone to leakage. On the other hand, hydrophilic drugs can only be kept in the interior of the vesicles or around the exterior periphery of the vesicles and mostly around the exterior periphery of the vesicles due to the difficulty in getting the drugs enter the vesicles, which is associated with poor stability and are prone to leakage. Liposomes of lipophilic drugs are significantly better than liposomes of hydrophilic drugs in terms of membrane permeability.

Thus, for hydrophilic drugs, if a lipid complex can be prepared first to improve lipophilicity, and then liposome vesicles can be prepared; this can improve entrapment efficiency and stability, and improve membrane permeability.

2. Research Background of Insulin-Lipid Complexes and the Defects of the Present Art 2.1 Research Background of Insulin-Lipid Complexes Insulin is susceptible to gastric acid and various proteolytic enzymes in the digestive tract and because of its big molecular weight, has difficulty penetrating the gastrointestinal barrier, normal oral preparations are ineffective, and subcutaneous injection is still the main route of administration, but long-term frequent injection in patients has poor compliance. To overcome the compliance problem with frequent injections, domestic and foreign medical workers have carried out a large number of research in the past few decades, on one hand preparing long-acting and intermediate-acting insulins through minor structural modifications, extending the maintenance time of the pharmaceutical effect, and reducing the quantity of injections, and on the other hand, to preparing liposomes and nanoparticles, microspheres, micro emulsions or oil solutions through pharmaceutical technology to improve acidity/alkalinity resistance of the drug and stability of the bio-enzyme, promote the transfer and absorption of drug through the epithelial mucosa, and to provide a sustained release drug carrier for the development of non-injectable drug preparations to be administered orally, percutaneously, via the mucosa, inhalation to the lungs, etc.

The insulin is lacking in lipophilicity, limiting the preparation and development of the microparticle support. Insulin liposomes are the most reported particulate carriers both at home and abroad, but with big molecular weight and strong hydrophilicity, most drugs exist in the periphery of the phospholipid bilayer, entrapment efficiency is low, are prone to leakage, and improvement of the stability of insulin in the gastrointestinal tract and mucosal permeability are limited. Moreover, the preparation of nanoparticles and microspheres is mostly in organic solvent systems, and insulin has poor solubility in organic solvents, low entrapment efficiency, is only adsorbed on the particle surface, is prone to release after drug administration, and the stabilization effect is likewise poor. The microemulsions or self-microemulsions reported in the existing literature, all make the insulin soluble in the aqueous phase so the drug is in contact with gastric acid and bio-enzymes, and do not improve the stability in the gastrointestinal environment.

The insulin molecule contains a large number of polar groups, such as acylaminos, phenolic hydroxyls, hydroxys, and carbonyls, all groups have the ability to generate intermolecular interactions with hydrophilic ends of lipid materials and form lipid complexes, thereby improving the lipophilicity, and breaking through the limits of microparticle carrier preparations. Research on insulin-lipid complexes has become the focus of attention at home and abroad in recent years. But the poor lipophilicity of insulin also limits the preparation of lipid complexes, and defects such as low recombination rate and variable quality were widely found in the domestic and foreign literature and patents.

2.2 The Shortcomings and Defects of the Current Art

Insulin is a protein consisting of two subunit polypeptides commonly referred to as the A-chain and the B-chain, and its molecular weight is close to 6000. The human Insulin (Insulin Human) A-chain has 21 amino acids of 11 kinds, and the B-chain has 30 amino acids of 15 kinds, for a total of 51 amino acids of 26 kinds. Insulin is insoluble in water and organic solvents, but soluble in acid diluted methanol, pH 7.4 phosphate buffer, low-concentration acid and low-concentration alkali.

Insulin contains a lot of polar groups and molecular interactions may occur between the hydrophilic ends of lipid materials, and meets the requirement to form lipid complexes. But the structural features and physical and chemical properties of insulin proteins make the preparation of lipid complexes extremely difficult, and the biggest obstacle is the choice of complex solvents.

Organic solvents, especially aprotic solvents, benefit recombination reactions, but insulin is insoluble in organic solvents and organic solvents may cause degradation or morphological changes in insulin, therefore, pure organic solvents can't prepare insulin complexes, and this has not been reported in the literature. If a pH7.4 phosphate buffer is chosen, insulin has certain solubility and stable quality, but the lipid materials cannot dissolve into clear transparent solution, and the polarity is too great to add to water, so entrapment efficiency of the complex obtained is extremely low, with weak intermolecular action, and unstable quality. Wo Weihan [Wo Weihan, recombinant human insulin complex, and its preparation methods and drug combination containing the complex, Chinese patent: 01140047,2004-10-06] using a phosphate buffer liquid as the solvent, dissolved or suspended insulin and phospholipids, respectively, in an aqueous solution, mixed it evenly, and removed water by freeze drying to prepare phospholipid complexes, and the results showed that, when the mass ratio of phospholipids and drug is 25:1(mole ratio is about 185:1), the recombination rate is only 21.35%, and when 150:1 (molar ratio is about 1110:1) the recombination rate is 72.0%.

Theoretically, insulin contains 53 acylamino groups, 4 phenolic hydroxyl groups, 12 alcoholic hydroxyl groups, and these groups are able to combine with phospholipids, and 1 mole of the drug needs about 70 moles of phospholipids in theory (the weight ratio is about 1:10). Usually, in order to ensure complete compounding of the drug, the feed volume of lipid material should be slightly higher than the theoretical value, at the 1.5 times of theoretical value, and the maximum amount of lipid material shall not exceed 15 times of drug mass that is, it is economical and reasonable that the phospholipid dosage should be controlled to ≤15 times the insulin mass. But in patent No. 01140047, when the mass of the phospholipid was as high as 150 times the insulin, it still cannot be fully compounded, which indicates that the compounding efficiency is too low with water as the solvent.

Another laid-open document [R•R•C•New, Hydrophobic preparation containing medium chain monoglyceride, Chinese patent: 97196069, 1999-07-28] the so-called Macrosol technique provides a insulin oil solution containing a lipid complex, and the preparation method for this lipid complex dissolves the drug and an amphipathic lipid material together in a buffer salt solution, and removes the solvent by rotary evaporation or freeze drying, and then dissolves it in an oil phase system to make an oil solution (or mixing the compound solution directly with oil, and then freeze drying). The determined weight ratio of insulin and phospholipids is 1:1 to 1:20, and 1:2 to 1:8 is preferred, however recombination rate evaluation results were not provided. In consideration of patent No. 01140047, it is difficult to obtain high recombination recombination rate with water as the solvent, and it is not hard to surmise that the preparation of complex under the conditions of patent No. 97196069, most of the drugs may not compound with phosphatides.

The inventor performed a verification of the method of patent No.97196069. First, the recombination rate determination method (HPLC Quantitative methods) was established according to characteristics that insulin complex is easy to dissolve in cyclohexane but free insulin is insoluble. Having prepared insulin phospholipid complexes according to method of patent No. 97196069, when the mass ratio of insulin/phospholipids is 1:2, the recombination rate was below 8%; when the mass ratio was 1:8, the recombination rate did not exceed 21%; when the mass ratio was 1:12, the recombination rate did not exceed 25%. When complexes of insulin/phospholipids with mass ratios of 1:8 and 1:12 were further dissolved in medium chain triglyceride oil, stirred to prepare medium chain triglyceride oil solutions with concentration of 1.5 mg/g, and kept at room temperature and for 1 month and in a refrigerator (2-8° C.) for 3 months, sediment appeared in all. Although mass ratios of insulin/phospholipids in patent No. 97196069 are close to the theoretical values, its preparation method used water as the complex solvent, and the recombination rate is very low, this is consistent with the results of the technology of patent No. 01140047.

Integrating the above two patents, they have the obvious flaw of preparing insulin-lipid complexes with water as the solvent, and the recombination rate is low.

The solvent system in some subsequent patents or reports, all implemented improvements based on patent No. 97196069, and selected solvents such as ethanol containing glacial acetic acid and DMSOs containing glacial acetic acid, or ethers containing HCl solution for the recombination reaction. Compared with aqueous solutions, organic solvents have relatively less polarity, and the addition of acid was to increase the solubility of insulin, and improve composite efficiency. The inventor has also performed verification tests and the results showed that, due to the strong acidity of glacial acetic acid and HCl, and their non-volatility, insulin content falls to 5-10% during the preparation, and continues to fall to 20% or more in storage. In addition, the mixture ratio of the drug and lipid materials has not been scientifically optimized, obtains complexes with low recombination rate and the improvement of the solubility in oil phase is limited, creates oil solutions with low drug loading capacity and manifests instability phenomena such as being prone to sedimentation in storage process, etc.

SUMMARY OF THE INVENTION

The present invention provides an insulin-lipid complex, compounded from insulin and lipid material in an organic solvent system containing a low boiling point acid, with the mass ratio of insulin and lipid material in the complex being 1:3~1:15; 1:4~1:12 being preferred; and 1:5~1:10 being more preferred.

The present invention provides an insulin-lipid complex, the insulin being selected from the group consisting of natural insulin, porcine insulin, bovine insulin, recombinant human insulin and intermediate-acting and long-acting insulin, recombinant human insulin is preferred; the lipid material is selected from the group consisting of natural phospholipids, synthetic phospholipids, cholesterol, cholic acid, salts thereof, and a combination thereof, natural phospholipids being preferred for the lipid material, and egg yolk phospholipid, or soybean phospholipid being preferred for the natural phospholipid.

The present invention provides an insulin-lipid complex, containing one or more ingredients selected from antioxidants, metal chelating agents and protease inhibitors.

The present invention provides an insulin-lipid complex, organic solvents used being complex solvents containing a low boiling point acid, wherein, the low boiling point acid is selected from the group consisting of trifluoroacetic acid, hydrogen chloride, and a combination thereof, and the organic solvent being selected from the group consisting of methanol, tetrahydrofuran, DMSO, chloroform, dichloromethane, ether and a combination thereof.

The following methods can be used to prepare the insulin-lipid complex of the present invention:

Method 1) take some organic solvent, add some trifluoroacetic acid first or some hydrogen chloride gas, then add the insulin and lipid material, stirring fully to compound and form a transparent solution, remove the organic solvent by rotary evaporation or the spray drying method, and drying.

Method 2) take some organic solvent, dissolve the lipid material in it, and add insulin, stirring while adding some hydrogen chloride gas or some trifluoroacetic acid to form a transparent solution, stirring or ultrasonic processing for a given time at room temperature, fully compound the insulin and lipid material, remove the organic solvent by rotary evaporation or the spray drying method, and drying.

Method 3) dissolve insulin in solvent A containing some trifluoroacetic acid or hydrogen chloride gas, to form a pellucid insulin solution, and dissolve lipid material in solvent B to form a pellucid lipid solution, mix the insulin solution and lipid solution even, and then perform reduced pressure distillation with a water bath, and remove the solvent by pumping, and drying.

Method 4) dissolve insulin in solvent A containing some trifluoroacetic acid or hydrogen chloride gas to form a pellucid insulin solution, and dissolve a lipid material in solvent B to form a pellucid lipid solution, mix the insulin solution and lipid solution with reduced pressure distillation under water bathing conditions and a given temperature, and slowly add some solvent B during the distillation process, and remove the solvent by pumping, and drying.

Said "organic solvent" in Method 1) and Method 2) is selected from the group consisting of methanol, tetrahydrofuran, DMSO, or a combination thereof, methanol being preferred. The added amount of trifluoroacetic acid and hydrogen chloride gas are preferably standardized on the insulin being completely dissolved thereby, the concentration of acid in the organic solvent being 0.01-0.5%, and preferably 0.05-0.1% (weight/volume, g/ml).

Said "solvent A" in Method 3) and Method 4) is selected from a group consisting of methanol, tetrahydrofuran, DMSO or a combination thereof, methanol being preferred; Said "solvent B" is selected from a group consisting of chloroform, dichloromethane or a combination thereof, dichloromethane being preferred. The concentration of TCA or hydrogen chloride gas in solvent A is about 0.01-0.5%, 0.05-0.1% being preferred. The dosage of solvent B is about 3-8 times of solvent A, 4-6 times being preferred.

Within the composite solution of insulin and lipid material, the concentration of insulin should be controlled to 0.5~30 mg/ml, 1.0~10.0 mg/ml being preferred. The "room temperature" in "stirring at room temperature or ultrasonic processing for a given time" should be controlled at 15° C.°C.~30° C., for example 15° C., 20° C., 25° C. or 30° C.; "given time" means within 30 min, for example 30 min, 20 min, 10 min or 5 min."

In the preparation method of this invention, the method for removing the organic solvent can be the rotary evaporation method, and also the freeze drying method, or another method to remove solvent and with no influence on the stability of drugs can be adopted. To remove the solvent by the rotary evaporation method below 40° C., and for example, it can be 35° C. and 30° C. or 25° C.

The present invention provides a formulation for an insulin oil solution, and it contains the insulin-lipid complex of this invention and oil. Wherein, the oil is selected from the group consisting of LCT (Long chain Triglyceride), MCT (Medium Chain Triglyceride), Glyceryl monooleate, ethyl oleate, isopropyl myristate or a combination thereof.

The oil solution containing the insulin-lipid complex of this invention is characterized by an emulsifier selectable from one or several of Tween 80, Span 20, Brij, Ethoxylated hydrogenated castor oil (Cremphor RH40), polyoxyethylated castor oil (Cremphor EL35) and Labrosal emulsifier being freely selected and added.

The oil solution containing an insulin-lipid complex of this invention can include one or several co-emulsifiers freely selectable from propanediol, PEG400 and Transcutol.

The oil solution containing an insulin-lipid complex of this invention can have a drug content of 12 mg/g, 10 mg/g, 8 mg/g, 6 mg/g, 5 mg/g, 4 mg/g, 2 mg/g or less.

The insulin-lipid complex of this invention is applied to the preparation of the insulin-lipid complex to prepare a sustained-release insulin injection.

The oil solution containing an insulin-lipid complex of this invention is applied to the preparation of a non-injectable formulation such as oral, percutaneous, mucosal, and lung-inhaled insulin.

The present invention provides a new insulin vesicle, containing an insulin-lipid complex and phospholipids, and can include one or more mixed surfactant such as Tween20, Span60, and the like, the average Particle Size is about 20 nm-200 nm.

The new vesicle containing the insulin-lipid complex of this invention, can be an aqueous dispersion, and powder made by freeze drying or spray drying.

The new vesicle containing the insulin complex of this invention, applies to the preparation of non-injectable formulations such as oral, percutaneous, mucosal, and lung-inhaled.

Compared to the existing art, the complex of the present invention has the following advantages:

1) organic solvent system containing low boiling point acid is used as the complex solvent: the complex solvent contains no water, the low boiling point trifluoroacetic acid and hydrogen chloride gas is easy to evaporate, provides an acidic environment for insulin to dissolve and shortens the volatilization time of the organic solvent. The selected organic solvent can ensure the complex solution clarification of insulin and lipid material, and the polarity can ensure the compound stability of the insulin and lipid material, which does not affect the mass stability of insulin, obtaining a complex with no acidic material or water residues, the recombination rate is more than 90%, drug content has no obvious changes in the process of preparation and storage.

2) Reasonable drug/lipid material dosage: Based on this composite solvent breakthrough, it is possible to obtain a completely compounded complex when the mass ratio of insulin and lipid material is 1:3~1:15. The lipid material dosage coincides with the theoretical value.

3) Preparation of stable oil solution: the complex significantly improves the oil solubility of insulin, with improved drug loading capacity, good stability with no turbidity during long-term storage, and physical properties and chemical properties are stable.

4) Preparation of stable new vesicles: the complex significantly improves the lipophilicity of insulin, making the drug distribution in the bilayer membrane of vesicle, markedly improving the stability of the drugs in gastric and intestinal juice, and mucosal transport rate.

Unless otherwise specified, the scientific and technical terms and names in this invention have the same meaning as the common understanding of persons skilled in the art which the invention belongs to; And, unless otherwise specified, the substances used herein and the quantities and proportions thereof, and the equipment, instruments, and preparation conditions can be understood as known to persons skilled in the art or as per the description.

PREPARATION EXAMPLE

Figure 1:
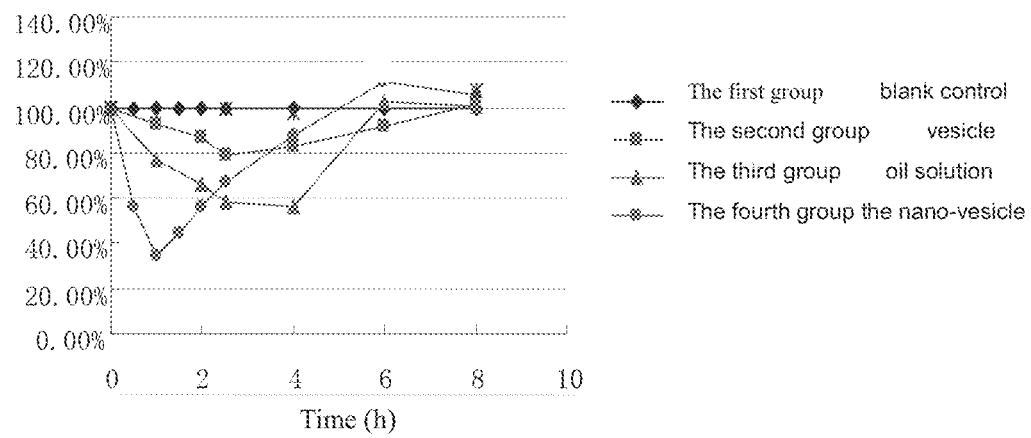
FIG. 1: Graph showing decrease of blood sugar by oil solution containing insulin-lipid complex and new vesicle.
Figure 2:
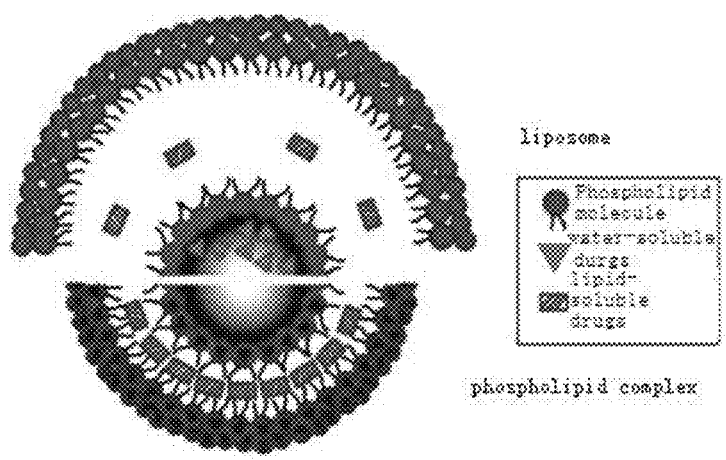
FIG. 2: Structural diagram of phospholipid complexes and liposome.

1. Early Exploratory Research Results 1.1 Discussion of the Effect of Organic Solvents on Chemical Properties and Spatial Structure of Drugs In earlier research work, the inventor investigated different organic solvents. The specific methods were as follows: take some insulin solution (pH7.4PBS), add an appropriate amount of methanol, ethanol, acetone, tetrahydrofuran, ethyl acetate, ether, chloroform, mix fully and place for 1 hour, dry by nitrogen flushing, add PBS solution (pH7.4) to redissolve, and after filtration, detect by HPLC, and compare with the same concentration of an insulin reference substance PBS solution, to calculate the change of insulin content. The results showed that the content of drug in methanol had no obvious change, and was the most stable, followed by tetrahydrofuran. Ethanol and acetone made drug content fall about 5-10%, ether: dropped about 15%, acetic ether, chloroform and tetrahydrofuran fell more markedly, about 30-40%. The chemical properties of insulin are relatively stable in the methanol and tetrahydrofuran. DMSO and DMF were also investigated. With their high boiling points, it was difficult to dry them by nitrogen flushing, so the freeze drying method was used to remove the solvent, and PBS solution (pH7.4) added to redissolve. After filtration, measurement was performed by HPLC as above to calculate the insulin content, the results showed that insulin content fell markedly in DMF, perhaps related to the alkaline conditions, and DMSO was relatively stable.

Further operating by the above method of methanol, tetrahydrofuran, and DMSO, after removing the solvent 5 mM PBS (pH7.4) is dissolved to create a test solution containing 0.1 mg/ml insulin, the test solution is placed in a quartz cuvette (optical path 0.1 cm) and assayed in the far-ultraviolet region (190 nm~250 nm) and the by circular dichromic spectroscopy, and the characteristic peaks and minimum ellipticity of the secondary structure map recorded. The other test solution was placed in a 1 cm cuvette, and assayed in the near-ultraviolet region (250 nm~350 nm), and the characteristic negative peak and minimum ellipticity of the tertiary structure map recorded.

The results showed having been treated by three kinds of solvents, the secondary structure map of the insulin showed two negative peaks, at 210 nm and 223 nm, respectively, and minimum ellipticity were −10.63 and −8.45; the tertiary structure map had a negative peak at 274.5 nm, minimum ellipticity was about −2.26. Compared to the results of the insulin PBS without organic solvent, there was no obvious change compared to the untreated insulin PBS, so methanol, tetrahydrofuran and DMSO will not lead to modifications in the spatial structure.

1.2 Influence on the Quality of Complex by Adding Glacial Acetic Acid and HCl

In the existing literature, most organic solvents are added to glacial acetic acid or HCl to make the insulin form a pellucid solution.

Glacial acetic acid has a high boiling point, its rotary evaporation is time consuming, and, the concentration of glacial acetic acid becomes more and stronger as the organic solvent volatizes, which causes insulin degradation. In particular, the remaining glacial acetic acid can't be removed in the final complex, harming the storage stability of the complex. This kind of complex with its relatively high residual volume of glacial acetic acid, still has a marked drop in drug content despite having been dissolve in oil solution, with the content usually dropping in the first 24 hours.

The inventor has chosen methanol as complex solvent which has no effect on the content of insulin content, added 1-5% glacial acetic acid, to prepare its complex with a drug/phospholipid mass ratio of 1:10, removed the solvent at 35° C. by the rotary evaporation method, dried for 48 hours under vacuum conditions, and assayed the complex. The recombination rate was more than 98%, but residues of glacial acetic acid exceeded 0.5% by gas chromatography. The complex was stored for 4 weeks at 2-8° C., and compared with the initial content, whereupon the insulin content had fallen about 20%. The complex was dissolved in medium chain triglycerides, and placed for 24 hours at room temperature, then compared with the initial content, whereupon the insulin content had fallen about 15%. So, the residual glacial acetic acid had a significant effect on product stability.

The inventor performed further testing with a methanol solution containing HCl as a reaction solvent and with the distillation method at 35° C. rotary evaporation (temperature is above 50° C. will significantly affect the quality of insulin, so it usually needs to be below 40° C., nor should the time be excessively long), the results showed that, due to the adding of water, it was more difficult to remove the solvent, and complex formation was poor. HCl residue was measured at about 0.2% by gas chromatography. The complex was stored for 4 weeks at 2-8° C., and thereafter compared with the initial content, the insulin content had fallen about 10%. The complex was dissolved in medium chain triglycerides, and placed for 24 hours at room temperature, then compared with the initial content, whereupon the insulin content had fallen about 5%.

1.3 Discussion on Methanol (Containing 0.1% trifluoroacetic acid)-dichloromethane as a Complex Solvent Using methanol (containing 0.1% trifluoroacetic acid)-dichloromethane as the solvent, and setting the drug concentration as 1.5 mg/ml, the feed ratios of insulin and soybean phospholipid was 1:1. 1:3, 1:5, 1:7.5, 1:10, 1:15 and 1:20 (w/w) respectively. The insulin was dissolved in methanol, dichloromethane added to the phospholipids, and mixed. The solvent was removed by rotary evaporation with a bath temperature was 37° C., and nitrogen flushing.

The recombination rate and solubility in oil phase were determined as follows:

Recombination rate (entrapment efficiency): The recombination rate was measured using the solubility of the insulin complex in C6H12, and the insolubility of free insulin in C6H12.

Determination of total drug content of the complex: A suitable volume of the insulin phospholipid complex was accurately weighed out, dissolved in methanol containing 1% glacial acetic acid a suitable volume of the insulin reference substance was dissolved in PBS solution (pH7.4) to prepare a solution (concentration of 1 mg/ml), and diluted in methanol containing 1% glacial acetic acid to make a 0.2 mg/mL solution as the reference solution. 10 μL of the test solution and reference solution were measured out respectively, and the total content (recorded as $W_{total}$) was assayed by by the HPLC method with 0.2% TFA: acetonitrile=70:30, column temperature 30° C., velocity 1 mL/min, wavelength of 214 nm, chromatographic column: Agilent ZORBAX 300 SB-C8.

Measurement of the complex content combined with phospholipids: A suitable volume of the insulin phospholipid complexes (containing about 10 mg insulin) was accurately weighed out, placed in a 10 mL volumetric flask, cyclohexane added, dissolved to constant volume, and shaken, the free insulin which was not compounded was filtered by 0.45 μm organic membrane, 2 mL of the subsequent filtrate was accurately measured out into a 10 mL volumetric flask, the solvent removed by nitrogen flushing, and methanol containing 1% glacial acetic acid added, dissolved to volume, shaken, and content measured by the above HPLC method, and drug content calculated by the external standard method, and recorded as $W_{composite}$.

The recombination rate was calculated according to the following formula: recombination rate %=($W_{composite}/W_{total}$)×100%

Solubility in oil: A suitable volume of the insulin and phospholipid complex was taken, soybean oil or medium chain Triglycerides added, stirred by a magnetic stirrer at 30° C. for 6 h to mix and dissolve, and placed at 30° C. for 24 h, and observed as to whether the drug was separated out. If no drug was separated out, insulin phospholipid complex was added, and the same operation performed until the drug is separated out. 5 ml were sampled and filtered by 0.45 μm membrane filtration, and the subsequent filtrate diluted with 1% acetate and methanol as appropriate, measured HPLC, and the apparent solubility in the soybean oil and medium chain triglycerides calculated.

The results of 7 groups of complexes are shown below:

Influence of ratio of drug and phospholipids on the complex

| insulin: phospholipids | content (%) | recombination rate (%) | medium chain solubility in oil (mg/g) |
| --- | --- | --- | --- |
| 1:1 | 86.34 | 4.48 | 0.116 |
| 1:3 | 91.23 | 9.76 | 1.492 |
| 1:5 | 94.77 | 98.5 | 2.39 |
| 1:7.5 | 96.17 | 97.3 | 7.83 |
| 1:10 | 98.31 | 96.0 | 7.09 |
| 1:15 | 98.74 | 96.6 | 6.59 |
| 1:20 | 97.82 | 93.2 | 6.71 |

The results show that the feed ratio of the drug to phospholipids has a significant influence on drug content, recombination rate and solubility. The content of the drug increases as the insulin drops in the system; when mass ratio of insulin and phospholipids is 1:5, the two compound completely, but if the ratio is above 1:15, the recombination rate enters in a downtrend. In medium chain triglycerides the solubility increases with the ratio of the phospholipids, and when the ratio is above 1:7.5, the solubility tends towards stability 1.4 Discussion of Using Methanol (With Hydrogen Chloride Gas) as a Complex Solvent Using methanol (with a suitable volume of hydrogen chloride gas) as complex solvent, drug concentration was set at 2 mg/ml, raw ratios of insulin and soybean phospholipid were 1:1. 1:3, 1:5, 1:7.5, 1:10, 1:15 and 1:20 (w/w) respectively. Insulin and lipid material were dissolved in methanol, stirred for 10 minutes at room temperature, the lipid material and drug dissolved to a pellucid solution, moved to a rotary evaporation flask, and the solvent removed by rotary evaporation at 35° C., reduced pressure distillation, and vacuum drying at room temperature for over 12 hours. The recombination rate and the solubility in oil phase were determined according to the method in Item 3.3 above, and the results were as follows:

Effect of ratio of drug to phospholipids on complex

| insulin: phospholipids | content (%) | recombination rate (%) | medium chain solubility in oil(mg/g) |
| --- | --- | --- | --- |
| 1:1 | 82.55 | 4.16 | 0.12 |
| 1:3 | 90.12 | 8.83 | 1.45 |
| 1:5 | 92.57 | 97.3 | 2.72 |
| 1:7.5 | 94.68 | 98.7 | 7.32 |
| 1:10 | 98.72 | 97.9 | 8.51 |
| 1:15 | 97.29 | 97.5 | 7.33 |
| 1:20 | 96.33 | 94.1 | 6.43 |

The purpose of this invention is to choose the appropriate complex solvent system, improve the compounding efficiency and quality stability of insulin and lipid material.

The selected solvent system can also meet the following requirements:
1) Lipid material and insulin can be dissolved to form a pellucid solution;
2) The system contains no water, with low polarity, benefitting intermolecular compounding between insulin and lipid material;
3) The solvent system has high evaporation efficiency, and easy vaporization without residual acid or water;
4) The insulin properties are stable in the preparation.

Example 1

Preparation of Insulin Complex Containing Different Ratios of Soybean Lecithin 0.2 g insulin was weighed out and put into a conical flask 9 times, 0.6 g, 1 g, 1.2 g, 1.4 g, 1.6 g, 1.8 g, 2.0 g, 2.4 g and 3.0 g soybean lecithin were added, respectively, then 20 ml methanol solution containing hydrogen chloride gas (concentration 0.1%, weight/volume, g/ml) was added, the mixture was stirred for 10 min at room temperature to dissolve the lipid material and drug to a pellucid solution, which was moved to flasks, and the solvent was removed by rotary evaporation, at 35° C., reduced pressure distillation and vacuum drying at room temperature for over 12 hours to obtain 9 groups of complex powders with drug/phospholipid weight ratios of 1:3~1:15 .

The 9 groups of complexes were assayed by gas chromatography and all were free of residual hydrogen chloride gas.

Example 2

Preparation of Insulin Complex Containing Different Ratios of Egg Yolk Lecithin 0.2 g insulin was weighed out and put into a conical flask 9 times, and 0.6 g, 1 g, 1.2 g, 1.4 g, 1.6 g, 1.8 g, 2.0 g, 2.4 g and 3.0 g egg yolk lecithin were added, respectively, then 20 ml methanol solution containing hydrogen chloride gas (concentration 0.1%, weight/volume, g/ml) was added, stirred for 10 min at room temperature to dissolve the lipid material and drug to a pellucid solution, which was moved to rotary evaporation flasks, the solvent was removed by rotary evaporation at 35° C., reduced pressure distillation and vacuum drying at room temperature for over 12 hours to obtain 9 groups of complex powders with drug/phospholipid weight ratios of 1:3~1:15.

The 9 groups of complexes were assayed by gas chromatography and all were free of residual hydrogen chloride gas.

Example 3

Preparation of Insulin Complex Containing Different Ratios of Soybean Lecithin 0.2 g insulin was weighed out and put into a conical flask 9 times, a suitable volume of methanol (containing 0.1%, v/v trifluoroacetic acid) was added to control the concentration of insulin to 10 mg/ml~2 mg/ml, and stirred at room temperature to dissolve the lipid material and drug to a pellucid solution; then 0.6 g, 1 g, 1.2 g, 1.4 g, 1.6 g, 1.8 g, 2.0 g, 2.4 g and 3.0 g soybean lecithin were taken, a suitable volume of dichloromethane (is about 3-6 times the methanol) added, then distilled under reduced pressure in a water bath at 37° C., a suitable volume of dichloromethane was added in the evaporation process (about 1-2 times the methanol), then switched to pump extraction for 10 min.

The 9 groups of complexes were assayed by gas chromatography and all were free of residual trifluoroacetic acid.

Example 4

Preparation of Insulin Complex Containing Different Ratios of Egg Yolk Lecithin 0.2 g insulin was weighed out and put into a conical flask 9 times, a suitable volume of methanol (containing 0.1%, v/v trifluoroacetic acid) was added, controlling the concentration of insulin to 10 mg/ml~2 mg/ml, stirred at room temperature to dissolve the lipid material and drug to a pellucid solution, then taking 0.6 g, 1 g, 1.2 g, 1.4 g, 1.6 g, 1.8 g, 2.0 g, 2.4 g and 3.0 g egg yolk lecithin, a suitable amount of dichloromethane (about 3-6 times the methanol) was added, then distilled under reduced pressure in a water bath at 37° C., a suitable volume of dichloromethane was added in the pressure distillation (about 1-2 times the methanol), then switched to pump extraction for 10 min.

The 9 groups of complexes were assayed by gas chromatography and all were free of residual trifluoroacetic acid.

Example 5

Preparation of Insulin Complex Containing Different Ratios of Sodium Deoxycholate 0.2 g insulin was weighed out and put in to a conical flask 8 times, 1 g, 1.2 g, 1.4 g, 1.6 g, 1.8 g, 2.0 g, 2.4 g and 3.0 g sodium deoxycholate were added respectively, then 20 ml tetrahydrofuran solution containing hydrogen chloride gas (concentration 0.1%, weight/volume, g/ml) was added, stirred for 5 min at room temperature and moved to rotary evaporator, and the solvent was removed by rotary evaporation at 35° C., reduced pressure distillation and vacuum drying at room temperature for over 12 hours. 8 groups of complex powder with drug/phospholipid weight ratios of 1:5~1:15 were obtained.

The 8 groups of complexes were assayed by gas chromatography and all were free of residual hydrogen chloride gas.

Example 6

Preparation of Insulin Complexes Containing Different Ratios of Sodium Deoxycholate 0.2 g insulin was weighed out and put to a conical flask 9 times, a suitable volume of methanol (containing 0.1%, v/v trifluoroacetic acid) was added, with the concentration of insulin contolled to 10 mg/ml~2 mg/ml, then stirred at room temperature to dissolve lipid material and drug to a pellucid solution then 0.6 g, 1 g, 1.2 g, 1.4 g, 1.6 g, 1.8 g, 2.0 g, 2.4 g and 3.0 g sodium deoxycholate were taken, a suitable amount of dichloromethane (about 3-6 times the methanol) was added, and distilled under reduced pressure in a water bath at 37° C., a suitable volume of dichloromethane was added to distillation (about 1-2 times the methanol), pumping for 10 min after drying.

The 9 groups of complexes were assayed by gas chromatography and all were free of residual hydrogen chloride.

Example 7

Preparation of Insulin Complex by DMSO (Instead of Methanol)

0.2 g insulin was weighed out and put to a conical flask 3 times, 2.0 g of soy phosphatidylcholine, egg yolk phosphatidylcholine and sodium deoxycholate were added, and 15 ml DMSO solution containing hydrogen chloride gas (concentration 0.1%, weight/volume, g/ml) was added, stirred at room temperature for 15 min, pre-frozen below −40° C. and the solvent was removed by freeze drying, obtaining 3 groups of complexes.

The 3 groups of complexes were assayed by gas chromatography and all were free of residual hydrogen chloride gas.

Example 8

Oil Solution Containing Insulin and Phospholipid Complex 1.8 g soy phosphatidylcholine was weighed out, 30 ml methanol solution was added, stirred to dissolve, 0.2 g insulin and hydrogen chloride gas were added until the solution was clear and transparent, stirred for 5 min at room temperature, and the solvent removed by rotary evaporation at 35° C., reduced pressure distillation and vacuum drying at room temperature for over 12 hours to obtain the complex.

0.3 g of the complex was weighed out 5 times, and to each, the following was added: 2.7 g of Glyceryl monooleate, medium chain Triglycerides (medium chain oils), ethyl oleate and isopropyl myristate; the mixture was stirred to dissolve, thereby obtaining an oil solution with 10 mg/g of drug loading capacity, which was then filtered.

Said oil solution was kept at room temperature for 24 hours until the solution was clear and transparent, the residual content was determined by HPLC to be 99.7% of the initial amount, which indicates that the drug was undegraded; the solution was kept at 2-8° C. for 6 months until the solution was clear and transparent, and the residual content was determined by HPLC to beis 99.1% of the initial amount, showing stable quality.

Example 9

Oil Solution Containing Insulin and Phospholipid Complexes

The complexes of Examples 1 to 4 (all samples with a drug/lipid ratio of 1:10, w/w) were weighed out, 2 each, medium chain triglycerides (medium chain oils) or long chain triglycerides (long chain oils) to 10 g were added, and stirred to dissolve thereby obtaining oil solutions with drug loads of 1 mg/g, 2 mg/g, 3 mg/g and 5 mg/g.

| Formulation Composition | Formula 1 | Formula 2 | Formula 3 | Formula 4 |
|---|---|---|---|---|
| Complex | Example 1 | Example 2 | Example 3 | Example 4 |
| Amount of complex | 110 mg | 220 mg | 330 mg | 550 mg |
| Drug loading capacity | 1 mg/g | 2 mg/g | 3 mg/g | 5 mg/g |

Added medium chain oils or long chain oils to 10 g, respectively, to prepare 8 samples Said oil solutions were kept at room temperature for 24 hours until the solutions were clear and transparent, and the residual contents were measured by HPLC, and all were more than 98.5% of the initial amounts, indicating that the drug was not degraded; these were kept at 2-4° C. for 6 months until the solutions were clear and transparent, and the residual contents were measured by HPLC and all were more than 99.4% of the initial amounts, showing stable quality.

Example 10

Oil Solution Containing Insulin and Phospholipid Complexes (Containing an Emulsifier)

10 g medium chain Triglycerides (medium chain oils) were weighed out in 3 groups, 1 g, 2 g and 4 g of Tween 80 were added, respectively, and shaken to form oil phase containing an emulsifier.

| Formula Composition | Oil phase 1 | Oil phase 2 | Oil phase 3 |
|---|---|---|---|
| MCT | 10 g | 10 g | 10 g |
| Tween 80 | 1 g | 2 g | 4 g |

MCT: Medium Chain Triglycerides

The complexes of Examples 5 to 7 (all samples with a drug/lipid ratio of 1:10, w/w) were weighed out into 3 groups in all, 9.45 g of each oil phase with different emulsifier ratios was added, stirred to dissolve to form an oil solution with capacity drug load of 5 mg/g, and filtered.

| Formula Composition | Formula 1 | Formula 2 | Formula 3 |
|---|---|---|---|
| Amount of complex were all 550 mg | Example 5 | Example 6 | Example 7 |
| Oil phase was 9.45 g | Oil phase 1 | Oil phase 2 | Oil phase 3 |

Said oil solutions were kept at room temperature for 24 hours until the solutions were clear and transparent, the residual contents were determined by HPLC to be more than 98.3% of the initial amounts, which indicates that the drug was undegraded; the solutions were kept at 2-4° C. for 6 months until the solutions were clear and transparent, and the residual contents were measured by HPLC and all were more than 97.7% of the initial amounts, showing stable quality.

Said oil solution contained an emulsifier, will be emulsified when 50 times water is added and magnetically stirred for 3 minutes, and the average Particle Size ≤1 μm after emulsification.

Example 11

Oil Solution Containing Insulin and Phospholipid Complexes (Containing an Emulsifier)

10 g of medium chain Triglycerides (medium chain oils) were weighed out, and 1 g, 2 g and 4 g of Cremphor RH40 were added, respectively, and shaken to form 3 groups of oil phases with different emulsifier ratios.

| Formula composition | Oil phase 1 | Oil phase 2 | Oil phase 3 |
|---|---|---|---|
| MCT | 10 g | 10 g | 10 g |
| Cremphor RH40 | 1 g | 2 g | 4 g |

MCT: Medium Chain Triglycerides

The complexes of Examples 2 to 4 (all samples with a drug/lipid ratio of 1:10, w/w) were weighed out into 3 groups, 9.12 g of each of the oil phases with different emulsifier ratios were added, and stirred to dissolve to form oil solutions with a drug load of 8 mg/g, and filtered.

| Formula Composition | Formula 1 | Formula 2 | Formula 3 |
|---|---|---|---|
| Complex amount 880 mg | Example 2 | Example 3 | Example 4 |
| Oil phase was 9.12 g | Oil phase 1 | Oil phase 2 | Oil phase 3 |

Said oil solution was stored at room temperature for 24 hours until the solutions were clear and transparent, the residual contents were measured by HPLC, and all were more than 98.6% of the initial amounts, indicating that the drug was not degraded; these were stored at 2-4° C. for 6 months until the solutions were clear and transparent, the residual contents were measured by HPLC, and all were more than 99.2% of the initial amounts, showing stable quality.

Said oil solution contained an emulsifier, and was emulsified when adding 50 times water and magnetically stirred for 3 minutes, and the average Particle Size was ≤1 μm after emulsion.

Example 12

Oil Solution Containing Insulin and Phospholipid Complexes (Containing Emulsifier and Co-Emulsifier)

The complexes (with the ratio 1:10, w/w of drug to lipid) of Example 1 to 4 were weighted to 4 groups, oil, emulsifier and co-emulsifier were added based on the following table, the mixture was stirred to dissolve to form self-microemulsion concentrated solution with drug loading capacity of 10 mg/g.

| Composition | prescription 1 | prescription 2 | prescription 3 | prescription 4 |
|---|---|---|---|---|
| Complex amount 1100 mg | Example 1 | Example 2 | Example 3 | Example 4 |
| Cremphor RH40 | 4 g | 4 g | 4 g | 4 g |
| propanediol | 5 g | / | / | / |
| Transcutol P | / | 4.5 g | 4 g | 3.5 g |

Add MCT/LCT (1:1) solution to 10 g

The 4 groups of oil solutions were kept at room temperature for 24 hours until the solutions were clear and transparent, the residual contents were determined by HPLC, and all were more than 98.3% of the initial amounts, indicating that the drug was undegraded; these groups were kept at −4° C. for 6 months until the solutions were clear and transparent, the residual contents were determined by HPLC, and all were more than 97.8% of the initial, with stable quality.

4 groups of oil solutions contain emulsifier and co-emulsifier, will be emulsified instantly when adding 5-500 times of the water, HCl or pH6.8 buffer solution, the average Particle Size within 20~50 nm after emulsion determined by laser particle analyzer.

Example 13

Vesicle Solution Containing Insulin and Phospholipid Complexes

A suitable amount of the complexes of Examples 1 to 3 (all samples with a drug/lipid ratio of 1:10, w/w) was weighed out to a round-bottom flask, a suitable volume of free phospholipids was added (Free phospholipids content was the same as the phospholipids of the complex), 20 ml dichloromethane was added, and the complexes and phospholipids were dissolved, and vacuum distilled to control the concentration of insulin to 1 mg/mL-10 mg/mL, at a bath temperature of 37° C., and after drying to form a film, 10 m LPBS solution was added to hydrate for 1 h, forming multicellular vesicles, and these were treated by ultrasonic fractionation or High Pressure Homogenization, to form single vesicles with a Particle Size of 50 nm.

| Formula Composition | Formula 1 | Formula 2 | Formula 3 |
|---|---|---|---|
| Complex (Example 1-3) | Example 1 110 mg | Example 2 220 mg | Example 3 550 mg |
| Free phospholipids | 100 mg | 200 mg | 500 mg |

Example 14

Vesicle Solution Containing Insulin and Phospholipid Complexes

A suitable amount of complexes of Examples 1 to 8 (all samples with a drug/lipid ratio of 1:10, w/w) were weighed out into round-bottom flasks, a suitable amount of free phospholipids was added (Free phospholipids content was the same as phospholipids of the complex), a suitable amount of Tween20 or Span60 surfactant, or a combination thereof, was added, 20 ml dichloromethane was also added, the complexes and phospholipids were dissolved, then vacuum distilled with the insulin concentration controlled to 1 mg/mL-10 mg/mL at a bath temperature of 37° C., a film was formed after drying, 10 m LPBS solution was added to hydrate for 1 h, forming multicellular vesicles, which were treated by ultrasonic fracturing or High Pressure Homogenization, to form single vesicles with a Particle Size of 50 nm.

| Formula Composition | Formula 1 | Formula 2 | Formula 3 |
|---|---|---|---|
| Complex (Example 1-3) | Example 1 110 mg | Example 2 220 mg | Example 3 550 mg |
| Free phospholipids | 100 mg | 200 mg | 500 mg |
| Tween20 | 200 mg | 400 mg | 600 mg |

| Formula Composition | Formula 1 | Formula 2 | Formula 3 |
|---|---|---|---|
| Complex (Example 1-3) | Example 1 110 mg | Example 2 220 mg | Example 3 550 mg |
| Free phospholipids | 100 mg | 200 mg | 500 mg |
| Span60 | 200 mg | 400 mg | 600 mg |

Example 15

Vesicle Powder Containing Insulin and Phospholipid Complexes

This was obtained by freeze drying the vesicle solution of Examples 13 and 14.

Test Examples

Test Example 1

Stability of Oil Solution Containing Insulin Complex in Gastrointestinal Tract Test Samples: Insulin Solution (INS)
Supernatant fluid: Insulin complex (Phytosome) dissolved in water
Oil solution of Example 8~Example 12

The test samples were placed in artificial gastric juice containing 1% (weight/volume, g/ml) of protease, incubated in a bath temperature of 37° C., and after vortex blending, 0.5 ml samples were taken at 1 min, 5 min, 30 min and 60 min, add 0.1 ml of cold Tris solution (take Tris reagent 6.07 g, added water to the 500 ml), centrifuge at 10000 RPM, 5 min, and after vortex blending, obtained the supernatant fluid, and the residual percentage of insulin measured by HPLC as above, the results were as follows:

| Sample | 1 min | 5 min | 30 min | 60 min |
| --- | --- | --- | --- | --- |
| Insulin solution (INS) | 0.56% | can't be detected | can't be detected | can't be detected |
| Insulin complex (Phytosome) | 50.4% | 35.4% | 28.4% | 12.4% |
| Oil solution of Example 8-Example 12 | Above than 87.2% | Above than 63.9% | Above than 43.7% | Above than 35.2% |

Test Example 2

Stability of Vesicle Solution Containing Insulin Complex in Gastrointestinal Tract Test Sample: Insulin Solution (INS)
Insulin vesicle (insulin instead of insulin complex, prepared as above)
New vesicle containing complex of Example 13

The test samples were placed in artificial gastric juice containing 1% (weight/volume, g/ml) of protease, incubated at a bath temperature of 37° C., and after vortex blending 0.5 ml samples were taken at 1 min, 5 min, 30 min and 60 min, 0.1 ml of cold Tris solution added (take Tris reagent 6.07 g, add water to the 500 ml), centrifuged at 10000 RPM, 5 min, and after vortex blending, the supernatant fluid, and obtained and the residual percentage of insulin measured by HPLC as above, and the results were as follows:

| Sample | 1 min | 5 min | 30 min | 60 min |
| --- | --- | --- | --- | --- |
| Iinsulin solution(INS) | 0.76% | Undetected | Undetected | Undetected |
| Insulin vesicle | 53.5-56.1% | 33.2-37.4% | 22.1-28.6% | 11.5-14.7% |
| Vesicle of Example 13 | 82.2-85.2% | 68.3-72.9% | 43.2-45.7% | 30.8-33.2% |

Test Example 3

Caco-2 Cell Permeability of Vesicle Solution Containing Insulin Complex

Test Sample: Insulin Solution (INS)
Insulin vesicle (insulin instead of insulin complex, prepared as above)
New Vesicle Containing the Complex of Example 13

0.5 mL of insulin solution of the same concentration was accurately weighed out, the insulin was encapsulated in the same vesicle as the insulin phospholipid complexes (Example 13), moved to 12 WL Caco-2 cells, 1.5 mL HBSS solution was added below the cells as acceptance medium, incubated at a bath temperature of 37° C., and took 200 μl samples at 30, 60, 120, 180 and 240 min, assayed by the HPLC method, the cumulative permeation amount was calculated, and the results were as follows:

| Sample | Cumulative permeation (%) |
| --- | --- |
| Insulin solution(INS) | 1.65 |
| Insulin vesicle | 8.70 |
| Vesicle of Example 13 | Above 17.52 |

Test Example 4

Oil Solution of Insulin Complex and Hypoglycemic Effect of New Vesicle

Normal male rats, weight: 200±20 g, were fasted for 12 h (Overnight), intraperitoneally injected with 10 mg/ml streptozocin-trisodium citrate buffer (pH is about 4.5) at 60 mg/kg for a week, and rats with blood sugar level more than 16.7 mmol/l were chosen for the diabetes model.

35 rats were fasted for a night, but not dehydrated, randomly divided into 5 groups and administered as follows, and blood sugar was examined after the injection.
The first group: blank control,
The second group: insulin vesicles, orally administered at 70 IU/kg
The third group: oil solution of formula 1 of Example 9 prepared by medium chain triglycerides, orally administrated at 70 IU/kg
The fourth group: new nanometer vesicles of Example 13, orally administrated at 70 IU/kg.

The blood sugar percentage of each animal was calculated at each point of time, and the Hypoglycemic effect curve drawn as shown in FIG. 1, with the hypoglycemic percentage as the Y-axis, and time as the X-axis.

What is claimed is:

1. A process for the preparation of an insulin-lipid complex, wherein the insulin-lipid complex is composed of insulin and lipid material and is not a liposome, the mass ratio of insulin to the lipid material being 1:3~1:20, the process comprising:
   (i) combining and mixing an organic solvent, a low boiling point acid, insulin, and a lipid material, wherein the organic solvent is selected from the group consisting of methanol, tetrahydrofuran, DMSO, chloroform, dichloromethane, and combinations thereof, and the low boiling point acid is selected from the group consisting of trifluoroacetic acid and hydrogen chloride gas, or a combination thereof;
   (ii) stirring to result in complexing of the insulin and lipid material; and
   (iii) removing the organic solvent.

2. The process for the preparation of an insulin-lipid complex according to claim 1, wherein said insulin is selected from the group consisting of natural insulin, porcine insulin, bovine insulin, recombinant human insulin and medium or long-acting insulin; and said lipid material is selected from the group consisting of natural phospholipids, synthetic phospholipids, cholesterol, cholic acid and salts thereof.

3. The process for the preparation of an insulin-lipid complex according to claim 2, wherein said insulin is recombinant human insulin, said lipid material is natural phospholipids, and the mass ratio of insulin to the natural phospholipids is 1:5~1:10.

4. The process for the preparation of an insulin-lipid complex according to claim 1, wherein said insulin-lipid complex further contains at least one selected from the groups consisting of antioxidants, metal-chelators, and protease inhibitors.

5. The process according to claim 1,
   wherein the combining in step (i) comprises combining the organic solvent and the low boiling point acid to form a solution, and then adding the insulin and the lipid material to the solution;

wherein the stirring in step (ii) is performed to result in complexing of the insulin and lipid material and until the solution turns transparent;

wherein the removing in step (iii) is done by rotary evaporation or spray drying to leave a residue; and wherein the organic solvent is selected from the group consisting of methanol, tetrahydrofuran, and DMSO, or a combination thereof.

6. The process according to claim 5, further comprising:
(iv) drying the residue produced in step (iii).

7. The process according to claim 1, wherein the concentration of the low boiling point acid in the organic solvent is between 0.01% g/mL and 0.5% g/mL.

8. The process according to claim 1, wherein the concentration of the insulin in the mixed solution of the insulin and the lipid is 0.5~30 mg/mL.

9. The process according to claim 1, wherein stirring is conducted at 25° C. to 30° C.

10. The process according to claim 5, wherein rotary evaporation is conducted at 25° C. to 40° C.

\* \* \* \* \*